United States Patent
Hoftman

(10) Patent No.: US 7,441,655 B1
(45) Date of Patent: Oct. 28, 2008

(54) TRANSFER TRAY FOR SURGICAL SHARPS

(76) Inventor: Mike Hoftman, 22205 Dardenne Ave., Calabasas, CA (US) 91311

( * ) Notice: Subject to any disclaimer, the term of this patent is extended or adjusted under 35 U.S.C. 154(b) by 214 days.

(21) Appl. No.: 11/096,551

(22) Filed: Apr. 1, 2005

(51) Int. Cl.
*B65D 85/28* (2006.01)

(52) U.S. Cl. .................... 206/380; 206/370; 206/564

(58) Field of Classification Search ............... 206/63.3, 206/352, 363–366, 370, 380, 438, 485, 564; 211/60.1, 85.13; 220/23.4
See application file for complete search history.

(56) References Cited

U.S. PATENT DOCUMENTS

| | | | |
|---|---|---|---|
| 3,013,656 A | | 12/1961 | Murphy, Jr. |
| 4,969,554 A | | 11/1990 | Sawaya |
| 5,339,955 A | * | 8/1994 | Horan et al. ............... 206/370 |
| 6,047,826 A | * | 4/2000 | Kalinski et al. ............ 206/365 |
| 6,065,596 A | | 5/2000 | Cavanagh |
| 6,142,305 A | * | 11/2000 | Sembach .................... 206/701 |
| 6,142,440 A | * | 11/2000 | Gratz et al. ................ 206/564 |
| 6,206,260 B1 | * | 3/2001 | Covell et al. .............. 206/564 |
| 6,216,885 B1 | * | 4/2001 | Guillaume ................ 211/85.13 |

* cited by examiner

*Primary Examiner*—Luan K Bui

(57) ABSTRACT

The present invention is a dual function transfer tray that can be used for either a scalpel or a suturing needle holder with suturing needle. A scalpel slot is formed in the bottom of a relatively deep set of sloped walls. A suture needle cavity is formed above the first slot. However, at a mid-section of the scalpel slot and the half-cylindrical suture needle cavity are opposing and deep V-shaped cutaway sections in the sidewalls with a flat floor section between them. A user need never have to focus their attention for more than a split second to discern the location of the mid-section of the transfer tray. The user's thumb and forefinger are aimed at the V-shaped sidewall openings to grasp a midsection of a supported surgical sharps. The scalpel slot and half-cylindrical suture needle cavity are set relatively deep with respect to top edges of the transfer tray and the to form an open tray to prevent a user from being inadvertently injured by a scalpel blade or a suture needle. In addition, the scalpel cannot be placed in the scalpel slot unless it rests on one of its longitudinal edges, preferably the same one as that of its blade edge. Thus, a user grasping the mid-section of the scalpel handle in the cutaway and flat floor section picks up the scalpel in a ready-to-use position.

15 Claims, 6 Drawing Sheets

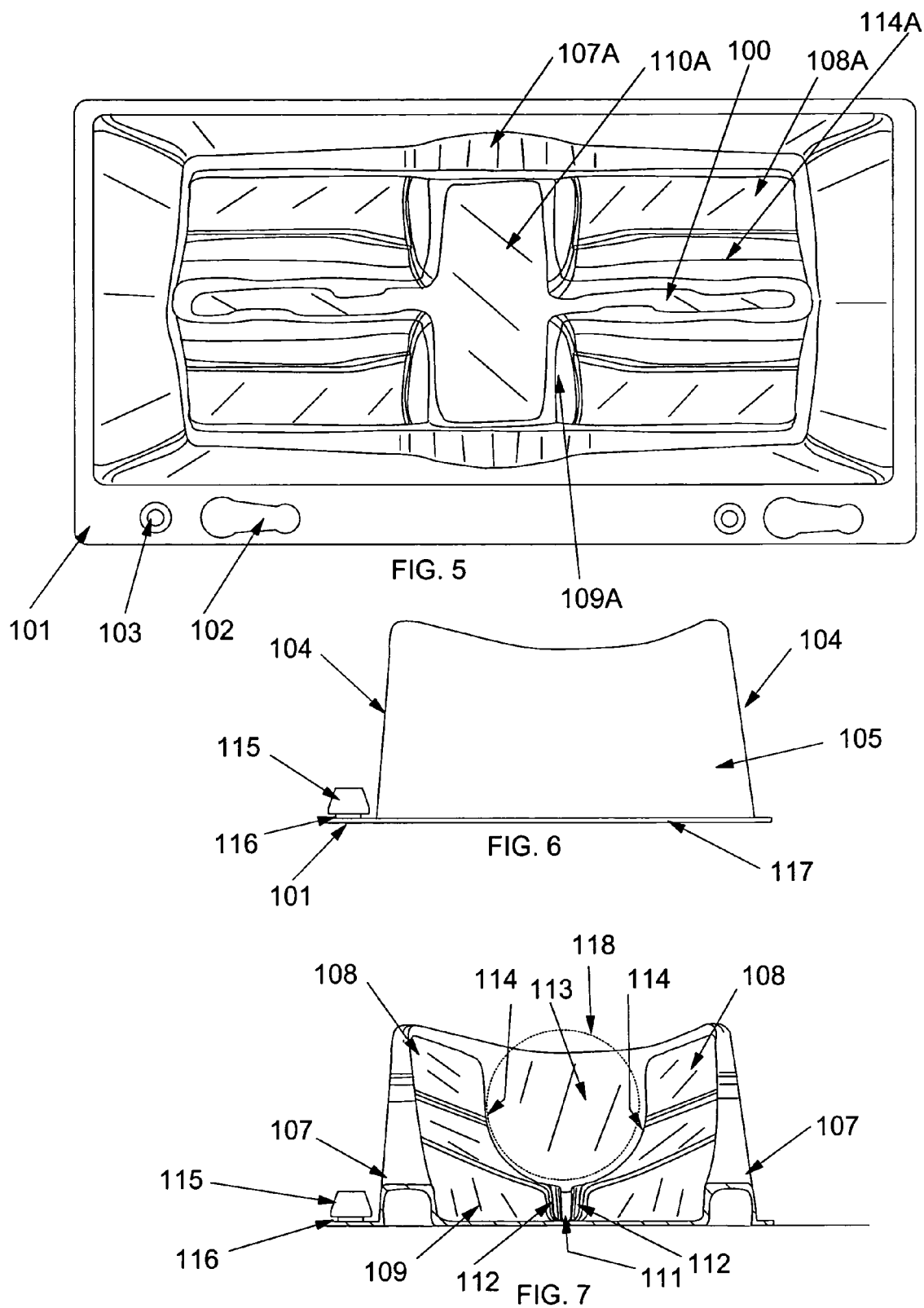

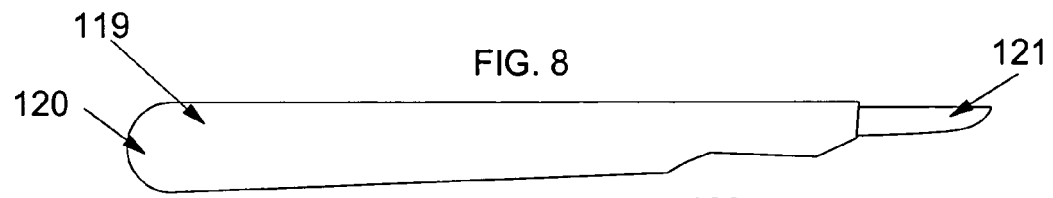
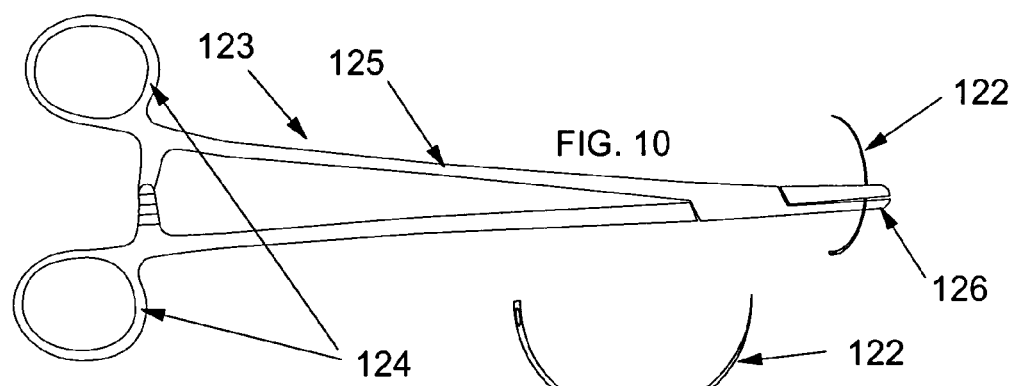

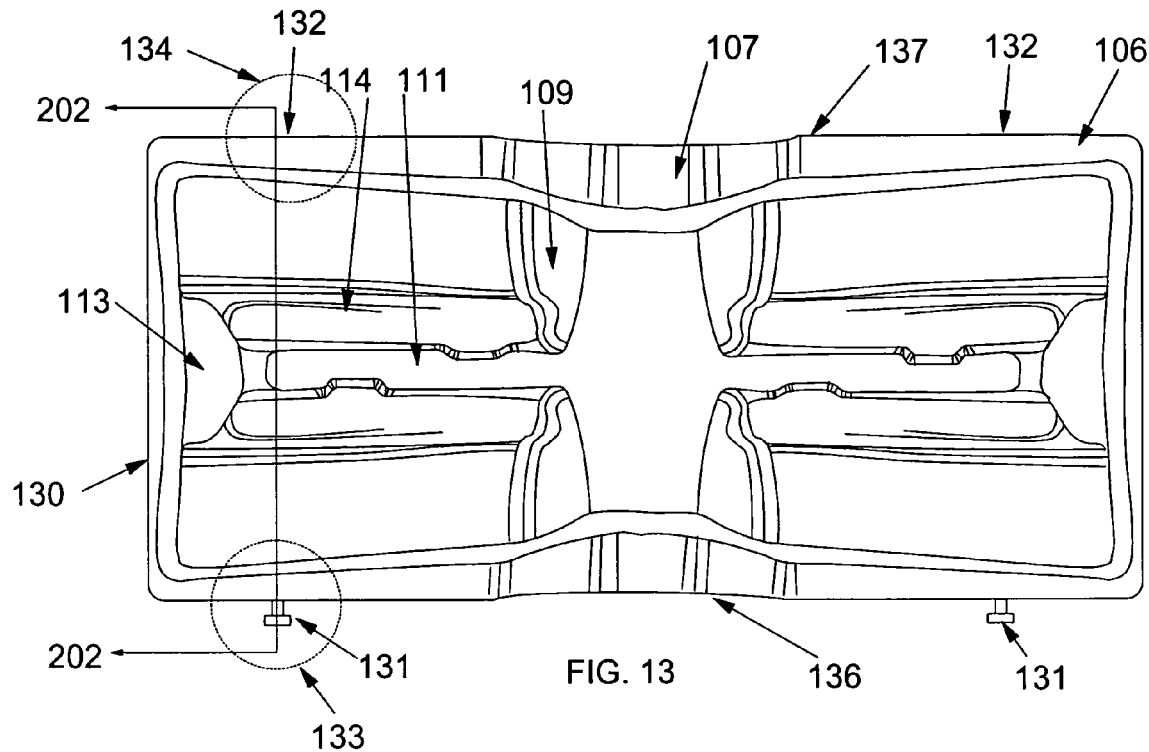
FIG. 13
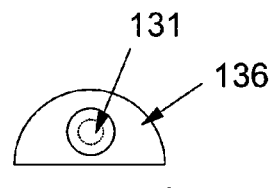
FIG. 14
FIG. 15
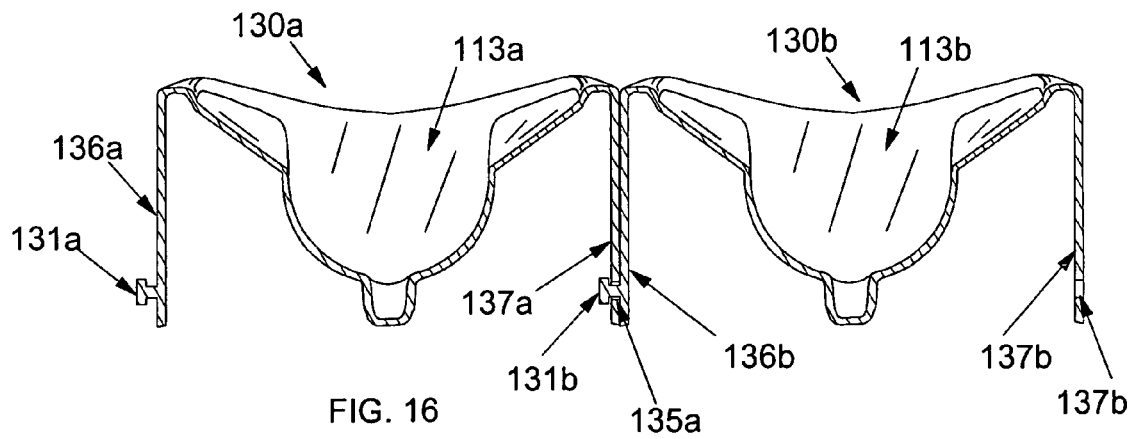
FIG. 16

TRANSFER TRAY FOR SURGICAL SHARPS

BACKGROUND OF THE INVENTION

The present invention relates to transfer trays for surgical sharps, especially those having a concavity for securing said sharps.

In surgical procedures, surgical sharps are passed between operating room personnel. The most important of these transfers is the one delivering the sharps piece to the operating surgeon. The surgeon's intense attention is focused on the portion of the patient's body to be addressed by the surgeon. Passage of surgical sharps to a necessarily distracted surgeon has in the past resulted in puncture or cutting wounds to the surgeon as he or she reaches for a surgical sharp piece.

In an attempt to reduce the likelihood of surgeon injury during passage of surgical sharps, one prior art device comprises an open topped kidney shaped dish fitted with slightly elevated ribs at the dish bottom. The surgical sharp piece is simply placed in the dish concavity so that the piece is supported by parallel ribs. A slight tilt of the dish to one side of the other by the transferring personnel results in the surgical sharps piece being dumped on the floor or in the surgical field. In addition, a user reaching into the dish is not provided with any protection from injury. While this device is somewhat superior to simply handing the piece to a surgeon, it is only a slight improvement.

U.S. Pat. No. 6,065,596 discloses two passing trays for two different types of surgical sharps. A first device has a rectangular opening with sloping side walls to a bottom longitudinal slot, which slot is expanded at a mid-section area so that a user's hand is somewhat directed to a mid-section of a scalpel handle of a scalpel located in the slot. There are important deficiencies with the '596 patent's first device for passing a scalpel. The scalpel handle rests on its side so that the user must (1) use slippery, glove-tipped fingertips to lift an edge of the scalpel handle and (2) re-orient the handle to cause the blade to face downward in order to actually use the scalpel. Second, a user must substantially re-direct their focus from a surgical site to the details of the first device tray in order to direct their fingers to the expanded part of the tray's long slot that will allow the user to pick up the scalpel. The user is protected from the scalpel blade because the scalpel lies flat on its side, i.e., the scalpel blade edge is directed to one of the side walls of the tray slot. However, the price paid for safety is inconvenience. A second device supports a suturing needle holder and suturing needle. There is no relationship between the first and second devices except that they are rectangular. The suturing needle holder in the second device is primarily supported on its two long shafts on an inclined plane so that the weight of the device causes it to slide slightly forward in a slot prepared for a semi-circular or curved needle. The slot of the second device still allows for puncture wounds to occur where the needle rises above the upper edges of the slot for the needle.

U.S. Pat. Nos. 3,013,656 and 4,969,554 also show that the prior art has contemplated the use of a concavity in disposable transfer trays for surgical sharps. However, a user must carefully direct their attention and visual focus to the tray concavity to be certain of the required location of thumb and fingers to grasp said sharps.

It is critical that a device used to transfer surgical sharps such as scalpels and suturing needle holders (with suturing needles) be presented in a transfer tray requiring only minimum attention by the user surgeon and providing a high level of protection against puncture and cutting injury to the surgeon's hand. The present invention provides those functions in this single device capable of bearing multiple types of surgical sharps.

SUMMARY OF INVENTION

The present invention is a dual function transfer tray that can be used for either a scalpel or a suturing needle holder with suturing needle. A scalpel slot is formed in the bottom of a relatively deep set of sloped walls. A half-cylindrical suture needle cavity is formed above the first slot. However, at a mid-section of the scalpel slot and the half-cylindrical suture needle cavity are opposing and deep V-shaped cutaway sections in the sidewalls with a flat floor section between them. A user need never have to focus their attention for more than a split second to discern the location of the mid-section of the transfer tray. The user's thumb and forefinger are aimed at the V-shaped sidewall openings to grasp a midsection of a supported surgical sharps. The scalpel slot and half-cylindrical suture needle cavity are set relatively deep with respect to top edges of the transfer tray to form an open tray to prevent a user from being inadvertently injured by a scalpel blade or a suture needle. In addition, the scalpel cannot be placed in the scalpel slot unless it rests on one of its longitudinal edges, preferably the same one as that of its blade edge. Thus, a user grasping the mid-section of the scalpel handle in the cutaway and flat floor section picks up the scalpel in a ready-to-use position.

Two handle surfaces are located at each end of the transfer tray (four total) and slope downward toward the mid-section of the transfer tray. The handle surfaces are continuous from upper edges of the half-cylindrical suture needle cavity so that the four surfaces are separated by the half-cylindrical suture needle cavity and the flat floor section. On the handle surfaces on one side of the flat floor section will rest the two ring handle ends of a suturing needle holder straddling opposite sides of the half-cylindrical suture needle cavity. Shafts of the needle holder that extend from the ring handles are angled downward over the flat floor section and converge to lie within an opposite portion of the half-cylindrical suture needle cavity. The other end of the needle holder comprises jaws of the device closed together to hold a suturing needle. The end of the jaws abut an end wall and the half-cylindrical suture needle cavity is adapted so that the suture needle lies within it safely below the upper level of the transfer tray.

Thus, a needle holder's own weight urges it down the handle surfaces of one end of the transfer tray toward an end wall at the other end of the transfer tray. The suturing needle is in this manner urged toward the end wall and is protectively supported within the half-cylindrical suture needle cavity. The jaws-end of the needle holder stops downward sliding of the needle holder.

The invention transfer tray can be used to safely transport and transfer essentially any scalpel or needle holder bearing a suturing needle so that a user cannot be harmed if they direct their thumb and fingers to opposite V- or other shaped deep cutaways in the sidewalls at the mid-section of the transfer tray.

The sharps piece after use can be very easily replaced in the transfer tray to be easily accessible for re-use during surgical procedures.

In a particularly important advantage, a surgeon need not even look at the transfer tray to safely pick up a scalpel or needle holder from the invention transfer tray. The cutaway portions of the long sidewalls are so dramatically different in elevation than the other top edges of the tray that a user can tell where to direct their thumb and fingers by simple detection of the cutaway sections by touch. A user knowing generally where the tray is located can place their palm and fingers in that area and quickly by touch detect the broad cutaway parts of the mid-section of the tray. The user can direct their thumb and forefingers to the opposite sides of the cutaway parts and instantly close in on the desired sharps piece. In the instant invention, a sharps piece may also be a pair of scissors or other ring-handled instrument with a sharp or cutting end.

In a preferred embodiment, the scalpel slot comprises two co-linear slot sections separated by the flat floor section in the mid-section of the tray. Each slot section comprises opposing slot walls spaced apart only sufficiently to edgewise support a scalpel. In another more preferred embodiment, the slot walls are somewhat more spaced apart than the handle thickness of most scalpels to accommodate even the thickest handled scalpels. However, each wall of each slot section comprises an addition securing lug that projects inward from said wall. The securing lugs cooperate to provide adequate secure support for the thinnest handled scalpel and are sufficiently compressible so that the thickest handled scalpel may be impressed in the slot according to the objects of the invention.

The invention transfer tray is preferably disposable and comprises a continuous shell of polymer formed by injection molding or vacuum forming. The shell form of the invention is very light and strong due to the multiple variations in surface angles and curvature. The invention transfer tray in a shell form is stackable so that dozens may be stored in a relatively small space.

In another embodiment, at least one long side of a rectangular form of the invention tray is laterally extended to provide a platform in which are defined connector slots and connector pins. Two of the invention connector trays may be quickly and releaseably connected. One tray bears two connector pins and the other tray bears two connector slots. The connector pins on one tray are inserted in the connector slots of another tray and one tray is moved so that the connector pins lock into a secure position in the connector slots of the other tray. Two or more invention trays can be securely locked together side by side so that multiple surgical sharps can be offered to a surgeon without the need to fumble for a second tray.

The invention tray defines a scalpel slot adjacently underneath and parallel to a half-cylindrical suture needle cavity so that one tray can be used for multiple surgical sharps devices, from scalpels to syringes (in the half-cylindrical suture needle cavity) to scissors and needle holders with suture needles. The half-cylindrical suture needle cavity is capable of being formed with a rectangular or polygonal cross section instead of only half-cylindrical and accomplishing the objects of the invention. A critical object of the invention with respect to curved suture needles is for the half-cylindrical suture needle cavity to be adapted to be sufficiently wide enough to protectively support such that a user's fingers are substantially prevented from contacting the point. The present invention is a combines the safe handling of sharps in a sterile, surgical field. Surgical sharps according to the invention comprise scalpel handles and blade combinations including handles commonly used for scalpel blade numbers identified as handles 3, 4, and 7 and blades 10, 11, 15, 20 and 22; sharp ring-handled instruments such as iris scissors; K-wires; combinations of hypodermic syringes and their connected hypodermic needles; trocars of commercially available sizes; and all sizes of suture needle holders bearing suture needles.

The present invention tray improves the user's ability to recover a previously used surgical sharp piece. The surfaces in the invention tray are downward contoured at relatively steep angles so that when a surgical sharp is dropped on the tray with little care to align the piece to the tray, the piece will quickly slide down the concavity walls to be aligned into the protected overall concavity of the tray.

Another object of the invention is to provide slanted surfaces at one end of the tray in cooperation with a half-cylindrical suture needle cavity at the other end so that a suture needle on a needle holder will slide into the half-cylindrical suture needle cavity and come to rest against an end wall. The suture needle is thereby forced pushed far from the mid-section whose cutaway walls encourage the user to grasp a mid-section of the surgical sharp in the tray.

In another embodiment of the invention, thumb rests are provided at ends of the rectangular tray so that surgical room personnel can present the transfer tray to a surgeon by holding only the ends of the tray. Said personnel's hands are thereby removed from any position that might interfere with the surgeon's reach into said tray.

BRIEF DESCRIPTION OF THE DRAWINGS

FIG. 5 is a bottom view of the tray of FIG. 1.
FIG. 6 is an end view of the tray of FIG. 1.
FIG. 7 is a section 201 view of the tray of FIG. 3.
FIGS. 8 and 9 are respectively side and top views of a scalpel.
FIG. 10 is a side view of a suture needle holder bearing a curved or semi-circular needle, as shown in FIG. 11.
FIG. 13 is a top view of the tray of FIG. 1 without a bottom edge flange but including lateral joining means.
FIG. 14 is a side view of section 134 of a long sidewall of the tray of FIG. 13.
FIG. 15 is a side view of section 133 of a long sidewall of the tray of FIG. 13.
FIG. 16 are two trays as shown in FIG. 13 in cross section 202 and laterally and securely joined.

DETAILED DESCRIPTION OF THE INVENTION

The invention is now discussed with reference to the figures.

Figure 1:
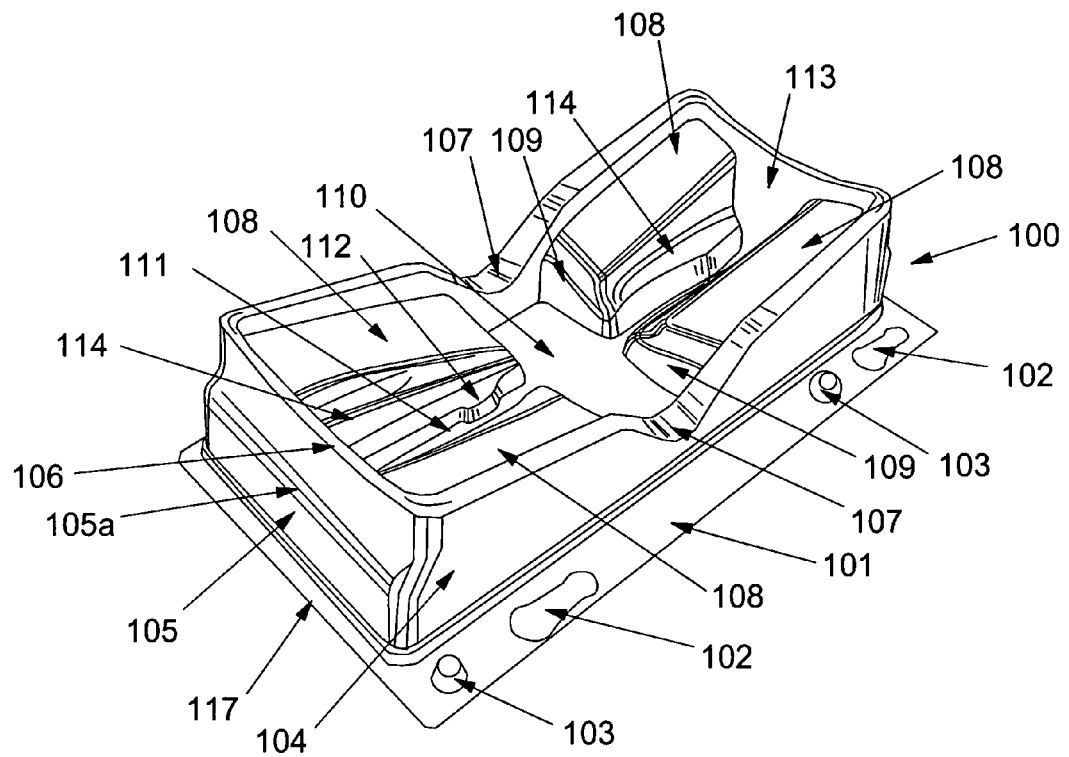
FIG. 1 is a top and perspective view of the invention tray.

FIG. 1 shows tray 100 comprising a rigid plastic shell formed by injection molding or vacuum forming. Tray 100 has significant concavities on the top and bottom sides. The concavities on the top side are adapted to securely support surgical sharps as defined above.

Figure 2:
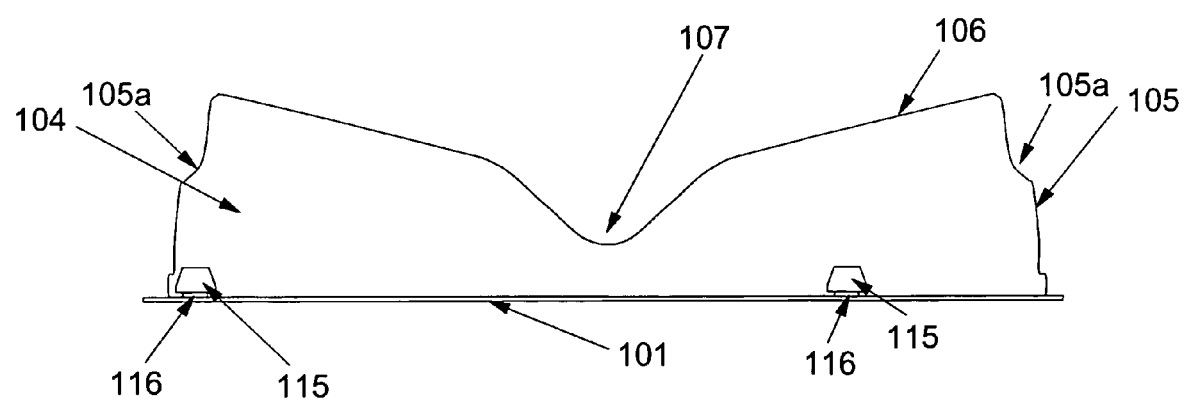
FIG. 2 is a side view of the tray of FIG. 1.
Figure 12:
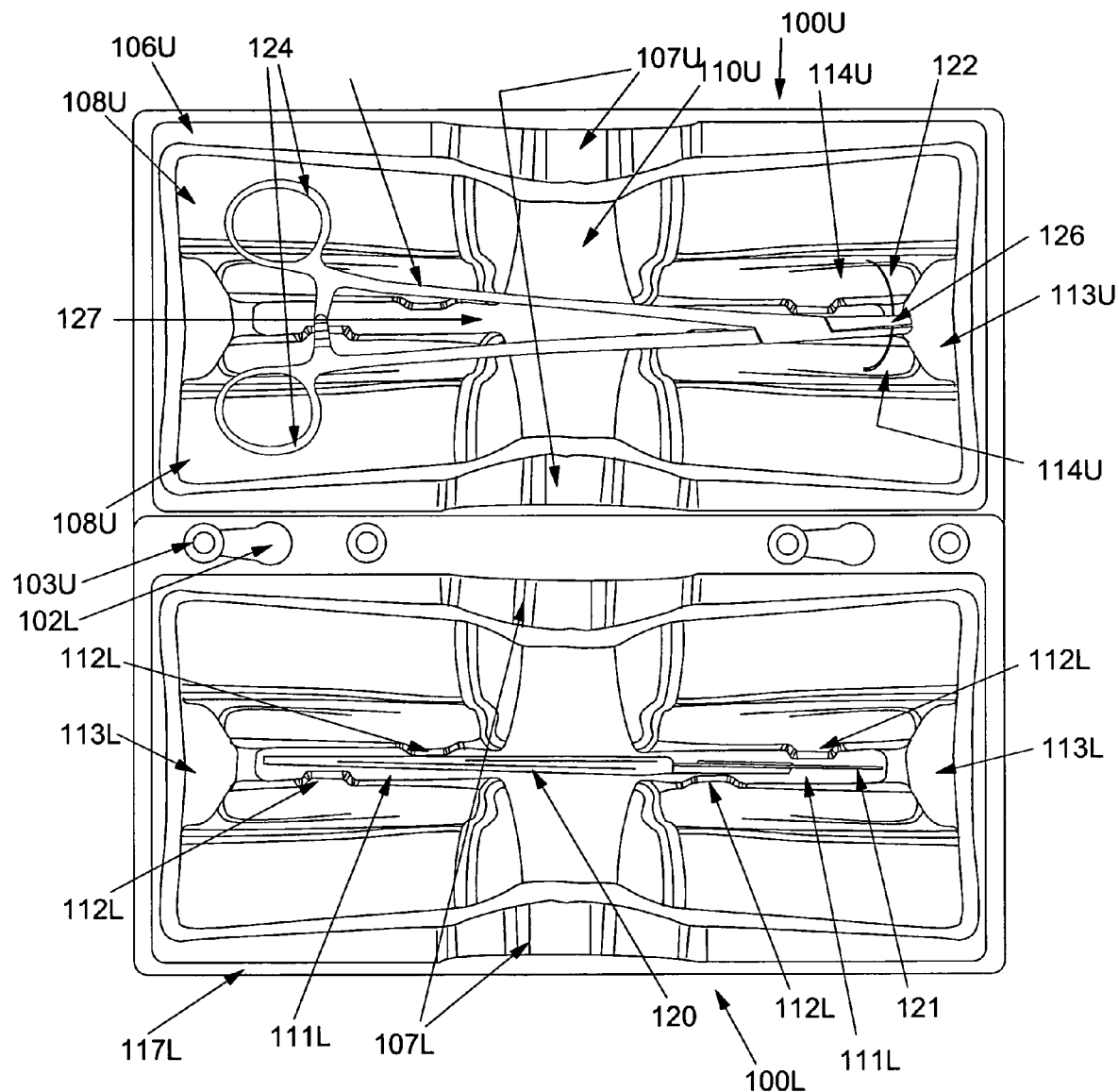
FIG. 12 is a top view of two adjacent and securely joined trays of FIG. 1, the upper tray supporting a suture needle holder and a suture needle of FIG. 10 and the lower, joined tray edgewise supporting the scalpel of FIG. 9.

Tray 100 comprises a bottom edge rim 117 on three sides and rim 101 on a long side of the rectangular shape of the tray. The rims 101 and 117 support the tray 100 when it is placed on a flat surface such as a tabletop. Rim 101 is sufficiently wide so that it accommodates lug slots 102 and lugs 103. As shown in FIGS. 2 and 6, lugs 103 comprise a top part 115 and neck part 116. To securely join two adjacent trays 100 in a side by side arrangement (as shown in FIG. 12), lugs 103U of the upper tray 100U are inserted into the lug slots 102L of lower tray 100L and tray 100U is moved longitudinally to the left in lug slots 102L until the neck parts 116 are secured in a left side of lug slots 102L.

Figure 3:
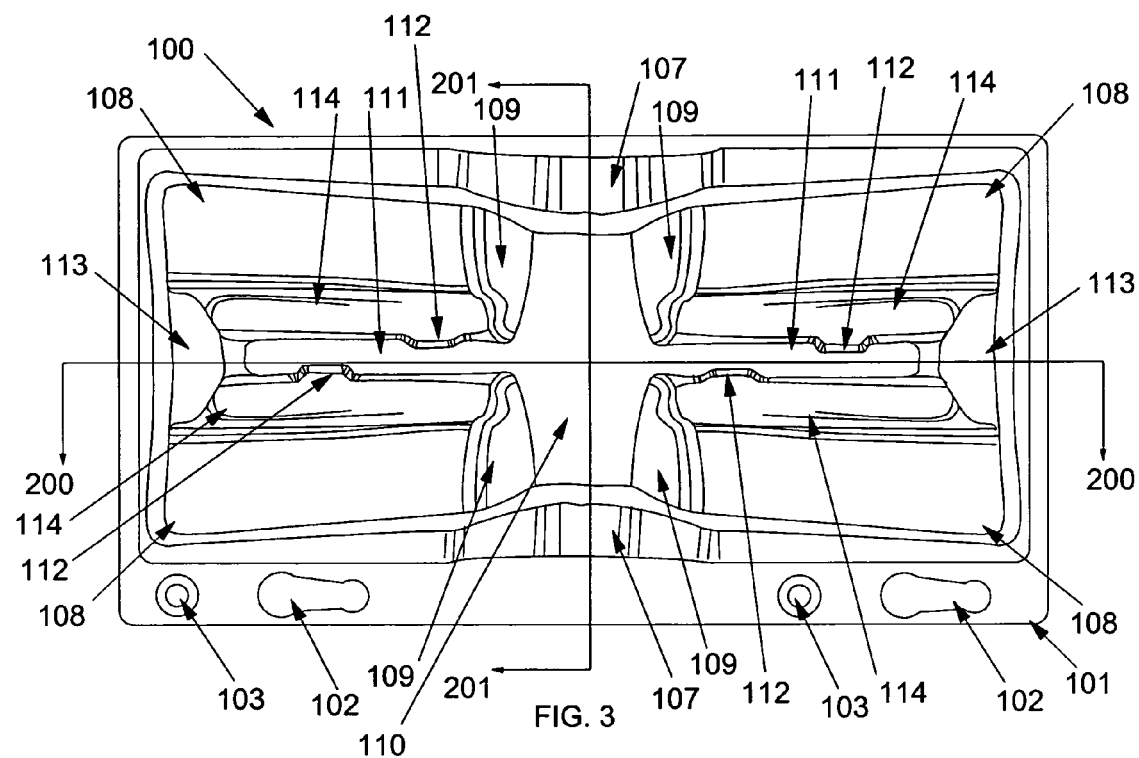
FIG. 3 is a top view of the tray of FIG. 1.
Figure 4:
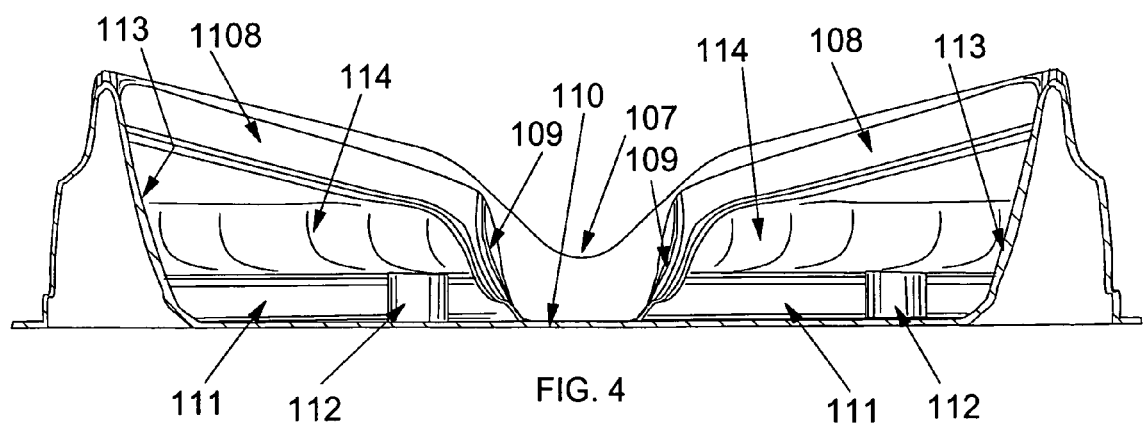
FIG. 4 is a section 200 view of the tray of FIG. 3.

FIGS. 1, 3 and 4 show that tray 100 further comprises two long outside walls 104 and two shorter outside walls 105. Outside walls 104 and 105 rise from rims 101 and 117 to a top edge 106 which forms a generally rectangular circumference of the tray 100 top concavities. In most significant and critical departure from the prior art, sidewall cutaways 107 reduce the height of outside walls 104 from a relatively high level at outside walls 105 to almost the elevation of a mid-section floor 110 only at the location of mid-section floor 110. Mid-section floor 110 is formed at about the same elevation as rims 101 and 117, is located at approximately the middle of the length of outside walls 104, and continuously spans the space between the cutaways 107. This particular construction is critical to many objects of the invention. Longitudinal extents of mid-section floor 110 are four mid-section walls 109 that rise from mid-section floor 110 so that each connects with an end of handle surface 108. The elevation of the connection of mid-section walls 109 and handle surfaces 108 is substantially below the connection of handle surfaces 108 with endwalls 113 so that each of the handle surfaces 108 is angled down from its connection with endwall 113 toward the mid-section floor 110.

The end outside walls 105 optionally are formed with substantial upward facing thumb ledges 105a (as in FIGS. 1 and 2). With ledges 105a, a person bearing tray 100 to the surgeon a surgical sharp can grasp tray 100 with an especially secure and safe grip as follows. Lateral end parts of rims 101 and 117 will rest on the outstretched and upward facing fingers and palms of two hands, i.e., a left hand at a left end of tray 100 and a right hand at the right end of tray 100. The bearer's thumbs extend upward over ledges 105a and the bearer presses their thumb tips downward onto ledges 105a, essentially clamping the tray 100 in the hands of the bearer. Even more important, every portion of the bearer's hands and fingers are located below the top edge 106 in the step where a surgeon retrieves or replaces a surgical sharp from tray 100. Keeping a user's hands below top edge 106 virtually eliminates the potential of puncture injury to the bearer. As sharps are moving back and forth in relation to tray 100, the bearer's hands are far below the motion paths of the surgical sharps.

Handle surfaces 108 and mid-section walls 109 are connected to an inner wall descending from an inner edge of to top edge 106. Handle surfaces 113 terminate at an inner edge to connect and descend downward to form suture needle walls 114. FIG. 7 shows that suture needle walls 114 generally define a semi-circular longitudinal cross section 118 (shown in broken lines). The diameter of cross section 118 is preferably from 0.5 to 3 inches to accommodate a curved or semi-circular suture needle held in the jaws of a suture needle holder. Each endwall 113 connects to pair of suture needle walls 113. Endwalls 113 are preferably sloped slightly inward from top edge 106.

In a preferred embodiment, suture needle walls 114 are divided at a longitudinal and lowest part at co-linear scalpel slots 111 separated by mid-section floor 110. Scalpel slots 111 are each formed from a pair of walls that rise from a floor part that is at the elevation of the mid-section floor 110. The height of the walls may be about more than one centimeter or that height sufficient to support edgewise the handle of a scalpel to be supported in slots 111. The space between the walls is less than the width of a scalpel handle or generally about 0.3 to 1.0 centimeters, or that width needed so that a scalpel placed in the scalpel slot will be forced to lay edgewise with only its edge on the floor of the scalpel slots 111 and the scalpel handle will abut one or both walls of scalpel slot 111. The space between scalpel slots 111 is the mid-section floor 110. The combined co-linear lengths of scalpel slots 111 and mid-section floor 110 are adapted so that a straight scalpel placed in scalpel slots 111 will lie with its ends between endwalls 113 and so that a mid-section of the scalpel handle is caused to extend across mid-section floor 110 with the rest of the scalpel lying in protective and secure enclosure between the walls of scalpel slots 111. A user can easily pass their thumb through one cutaway 107 and their fingers through the directly opposite cutaway 107 to grasp only the mid-section of a scalpel held securely in scalpel slots 111 but exposed across mid-section floor 110.

In an alternate embodiment as shown in FIGS. 3 and 7, scalpel slots 111 may have a spacer lug 112 extending inward from each of the walls of scalpel slots 111 to a distance of not more than about half the space between said walls. Spacer lugs 112 provide for flexibility in the vacuum forming process where the space between the opposing walls of slots 111 may not be formed sufficient close to obtain the objects of the invention related to slots 111. Spacer lugs 112 are formed with an extension into slots 111 that forms an effective width of slots 111 for a scalpel to be located therein.

FIGS. 8 and 9 show a scalpel 119 comprising a handle 120 and blade 121, common in most prior art designs. Handle 120 is relatively thin edgewise and broad in side view. FIG. 12 shows that scalpel 119 is located between endwalls 113L and protectively within scalpel slots 111L with a mid-section exposed across mid-section floor 110L.

Tray 100 also is capable of safely storing a suture needle holder 123 of FIG. 10 bearing a suture needle 122 of FIG. 11. Needle holder 125 comprises ring handles 124 that extend to shafts 125 and further to jaws 126. FIG. 10 shows that jaws 126 secure between them suture needle 122. If a user inadvertently places their hand near jaws 126, the user may sustain a puncture wound. It is critical that an transfer tray protect the user from such an injury. In the case of tray 100, FIG. 12 shows how that is accomplished. Ring handles 124 are placed on a pair of handle surfaces 108U with the jaws 126 directed to endwall 113U and between suture needle walls 114U. The weight of needle holder 123 causes the entire combination of needle holder 123 and suture needle 122 to slide in direction 127 toward the endwall 113U farthest from the ring-handle supporting handle surfaces 108U. The tip of jaws 126 comes to rest abutting an endwall 113U. The suture needle 122 lies entirely between to suture needle walls 114U in a protective valley formed thereby. In the similar manner as a user retrieving a scalpel from scalpel slots 111, a user can easily pass their thumb through one cutaway 107 and their fingers through the directly opposite cutaway 107 to grasp only the mid-section of the shafts of needle holder 123 which is supported on handle surfaces 108U and extending between a pair of suture needle walls 114 to protect the user from a puncture wound.

FIG. 5 shows the bottom side of tray 100. This view is essentially the features of the impressions made of the top side. Tray 100 is preferably formed from a substantially uniform sheet thickness of polymer. Thus, cutaway 107, handle surfaces 108, mid-section floor 110, scalpel slots 111, and suture needle walls 114 of FIG. 3 necessarily form their corresponding features of cutaway 107A, handle surfaces 108A, mid-section floor 110A, scalpel slots 111A, and suture needle walls 114A of FIG. 5.

It is an especially important feature of tray 100 that it can be used for all of its objects for securing and protecting a user from surgical sharps regardless of its lengthwise orientation. Scalpels and needle holders bearing suture needles are as effectively stored for access and transfer in tray 100 directed at either endwall 113 of said trays.

In a preferred embodiment, the reduction in elevation from the highest portion of sidewalls 104 to the lowest elevation of cutaway 107 is about one half or more of the highest portion of sidewalls 104.

FIGS. 13 through 16 show an alternate embodiment of joining means for two adjacent trays 130. The method of joining adjacent trays is similar to that of the tray of FIG. 1 although lugs 131 are directed horizontally and the lug slots 132 are formed in the vertical sidewall 137 in contrast to the vertical arrangement of lugs and lug slots in FIG. 1. FIG. 13 is a top view of the tray of FIG. 1, where two lugs 131 are fixed to and protrude horizontally from long sidewall 136. As shown in FIG. 14, lug slots 132 are formed in the other parallel, long sidewall 137, said lug slots 132 comprising a large opening end 138 and a small opening end 135 connected by a slide portion. Lugs 131 comprise a narrow neck part joining sidewall 136 and an expanded head part.

FIG. 16 shows tray 130a joined to tray 130b using the joining means of this embodiment. The head parts of each of two lugs 131b protruding from sidewall 136b of tray 130b have previously been inserted into the large opening ends 138a (not shown) of lug slots in sidewall 137a of tray 130a so that the outside surfaces of sidewalls 137a and 136b abut one another. Thereafter, trays 130*a* and 130*b* are moved longitudinally with respect to each other until the head parts of the lugs 131*b* are secured on the inside of sidewall 137*a* at the small opening ends 135*a* of the lug slots in that sidewall. Trays 130*a* and 130*b* can be disconnected by reversing these steps. This alternate embodiment of the joining means provides extremely secure connection of adjacent transfer trays and can be formed by injection molding at the same molding step as the rest of the tray 130.

The above design options will sometimes present the skilled designer with considerable and wide ranges from which to choose appropriate apparatus and method modifications for the above examples. However, the objects of the present invention will still be obtained by that skilled designer applying such design options in an appropriate manner.

I claim:

1. A transfer tray for surgical sharps comprising:
   (a) two parallel and substantially vertical outside length walls of equal lengths connected at their ends by outside end walls to form a box structure;
   (b) substantial side access cutaways defined at mid-sections of the outside length walls substantially reducing the height of said outside length walls by one half or more;
   (c) a floor section at about an elevation of the lowest edges of the outside length walls and extending between the outside length walls only between the side access cutaways and having two side to side edges;
   (d) mid-section walls rising to a first height from each of the two side to side edges of the floor section to a first elevation;
   (e) handle surfaces that extend up from the first elevation to a second elevation below top edges of the outside end walls, whereby the handle surfaces are sloped downward from the second elevation toward the floor section; and
   (f) opposing suture needle walls extend down from lengthwise edges of the handle surfaces and dividing the mid-section walls to a needle floor portion and defining two suture needle spaces therebetween to thereby form a pair of co-axial and longitudinal concavities.

2. The transfer tray of claim 1 wherein a longitudinal scalpel slot is defined in a lengthwise midline at the bottom of each of the suture needle spaces, so that the scalpel slots comprise four vertical walls extending down from said floor portions of opposing suture needle walls to a slot floor portion at the elevation of the mid-section floor, thereby defining two co-linear scalpel slots separated by the floor section.

3. The transfer tray of claim 1 wherein two handle surfaces at one lengthwise end of the transfer tray and a suture needle space distal to said the two handle surfaces are adapted to respectively support ring handles and the jaws bearing a suture needle of a suture needle holder comprising two ring handles and shafts extending from them to jaws securing between said jaws a curved or semi-circular suture needle, whereby.

4. The transfer tray of claim 3 wherein the suture needle space distal to said the two handle surfaces is adapted to have an effective depth greater than a highest end of the suture needle when it lies in the suture needle space distal to said the two handle surfaces.

5. The transfer tray of claim 4 wherein the vertical walls of the scalpel slots are separated by a space less than a major width of a handle of a scalpel.

6. The transfer tray of claim 5 wherein one or more spacer lugs extend from one or more of the vertical walls of the scalpel slots toward an opposing vertical wall thereof.

7. The transfer tray of claim 6 wherein the extension of the spacer lugs is one half or less of the entire width between said vertical walls of the scalpel slots.

8. The transfer tray of claim 1 wherein the device has been formed by vacuum forming.

9. The transfer tray of claim 1 wherein the device has been formed by injection molding.

10. A transfer tray for surgical sharps comprising:
    (a) a box structure with two endwalls of equal height and two longer sidewalls connecting the endwalls at box corners at about the same height as the endwalls at the box corners, where the longer sidewalls each have substantial side access cutaways defined at opposing mid-sections of the longer sidewalls substantially reducing the height of the longer sidewalls by one half or more;
    (b) a floor section at an elevation of lowest edges of the longer sidewalls and located below a space between the side access cutaways and having lengthwise edges generally parallel to the endwalls;
    (c) a pair of mid-section walls rising to a first height from each of the lengthwise edges of the floor section, each pair of mid-section walls separated equidistant from a lengthwise midline of the box structure;
    (d) handle surfaces that extend up from the first elevation to a second elevation below top edges of the outside end walls, whereby the handle surfaces are sloped downward from the second elevation toward the floor section; and
    (e) opposing suture needle walls that extend down from lengthwise edges of the handle surfaces to a needle floor portion thereby dividing the pairs of mid-section walls and defining two suture needle spaces therebetween to thereby form a pair of co-axial and longitudinal concavities.

11. The transfer tray of claim 10 wherein scalpel slots are defined along the lengthwise midline at the bottom of each of the suture needle spaces, so that the scalpel slots comprise four vertical walls extending down from said floor portions of the suture needle walls to a slot floor portion at the elevation of the mid-section floor, thereby defining two co-linear scalpel slots separated by the floor section.

12. The transfer tray of claim 10 wherein the vertical walls of the scalpel slots are separated by a space less than a major width of a handle of a scalpel.

13. The transfer tray of claim 11 wherein the vertical walls of the scalpel slots are separated by a space greater than a minor width of a handle of a scalpel.

14. The transfer tray of claim 13 wherein one or more spacer lugs extend from one or more of the vertical walls of the scalpel slots toward an opposing vertical wall thereof.

15. The transfer tray of claim 14 wherein the extension of the spacer lugs is one half or less of the entire width between said vertical walls of the scalpel slots.

* * * * *